(12) United States Patent
Deckman et al.

(10) Patent No.: US 7,815,571 B2
(45) Date of Patent: Oct. 19, 2010

(54) RIGID DELIVERY SYSTEMS HAVING INCLINED ULTRASOUND AND NEEDLE

(75) Inventors: Robert K Deckman, San Bruno, CA (US); Craig Gerbi, Mountain View, CA (US); Michael Munrow, Belmont, CA (US); Jessica Grossman, San Francisco, CA (US)

(73) Assignee: Gynesonics, Inc., Redwood City, CA (US)

( * ) Notice: Subject to any disclaimer, the term of this patent is extended or adjusted under 35 U.S.C. 154(b) by 545 days.

(21) Appl. No.: 11/409,496

(22) Filed: Apr. 20, 2006

(65) Prior Publication Data
US 2007/0249939 A1    Oct. 25, 2007

(51) Int. Cl.
*A61B 8/00* (2006.01)
*A61H 1/00* (2006.01)
*A61B 18/18* (2006.01)

(52) U.S. Cl. .......................... 600/439; 600/437; 601/2; 606/41; 606/46

(58) Field of Classification Search ....................... None
See application file for complete search history.

(56) References Cited

U.S. PATENT DOCUMENTS

| | | | |
|---|---|---|---|
| 4,289,132 A | 9/1981 | Rieman | |
| 4,936,281 A | 6/1990 | Stasz | |
| 5,372,587 A | 12/1994 | Hammerslag et al. | |
| 5,456,689 A | 10/1995 | Kresch | |
| 5,471,988 A | 12/1995 | Fujio et al. | |
| 5,492,126 A | 2/1996 | Hennige et al. | |
| 5,527,331 A | 6/1996 | Kresch et al. | |
| 5,531,676 A | 7/1996 | Edwards et al. | |
| 5,649,911 A | 7/1997 | Trerotola | |
| 5,666,954 A | 9/1997 | Chapelon et al. | |
| 5,697,897 A | 12/1997 | Buchholtz et al. | |
| 5,730,752 A | 3/1998 | Alden et al. | |
| 5,741,287 A | 4/1998 | Alden et al. | |

(Continued)

FOREIGN PATENT DOCUMENTS

WO    WO 97/17105    5/1997

(Continued)

OTHER PUBLICATIONS

Alterovitz et al., "Simulating Needle Insertion and Radioactive Seed Implantation for Prostate Brachytherapy," *Medicine Meets Virtual Reality* 11, Westwood et al. (Eds.), IOS Press, Jan. 2003, pp. 19-25.

(Continued)

*Primary Examiner*—Long V Le
*Assistant Examiner*—Angela M Hoffa
(74) *Attorney, Agent, or Firm*—Townsend and Townsend and Crew LLP

(57) ABSTRACT

A delivery system includes a rigid shaft, an imaging core, and an interventional core. The rigid delivery shaft has a proximal end, an angled distal tip, and an axial passage therethrough. The imaging core comprises an ultrasound imaging insert disposed within the axial passage. The imaging insert has an ultrasound array within a distal portion thereof, wherein the ultrasound array is tilted relative to a shaft axis. The interventional core comprises a curved ablation needle coupled to the rigid shaft. An angle of needle curvature may be inversely proportional to the ultrasound array tilt and tip angle.

31 Claims, 11 Drawing Sheets

U.S. PATENT DOCUMENTS

| | | | |
|---|---|---|---|
| 5,769,880 A | 6/1998 | Trukai et al. | |
| 5,860,974 A | 1/1999 | Abele | |
| 5,863,294 A | 1/1999 | Alden | |
| 5,873,828 A * | 2/1999 | Fujio et al. | 600/439 |
| 5,876,340 A | 3/1999 | Tu et al. | |
| 5,876,399 A | 3/1999 | Chia et al. | |
| 5,891,137 A | 4/1999 | Chia et al. | |
| 5,906,615 A | 5/1999 | Thompson | |
| 5,916,198 A | 6/1999 | Dillow | |
| 5,957,941 A | 9/1999 | Ream | |
| 5,964,740 A | 10/1999 | Ouchi | |
| 5,979,452 A | 11/1999 | Fogarty et al. | |
| 5,979,453 A | 11/1999 | Savage et al. | |
| 5,984,942 A | 11/1999 | Alden et al. | |
| 6,002,968 A | 12/1999 | Edwards | |
| 6,007,499 A | 12/1999 | Martin et al. | |
| 6,032,673 A | 3/2000 | Savage et al. | |
| 6,039,748 A | 3/2000 | Savage et al. | |
| 6,059,766 A | 5/2000 | Greff | |
| 6,077,257 A | 6/2000 | Edwards et al. | |
| 6,141,577 A | 10/2000 | Rolland et al. | |
| 6,146,378 A | 11/2000 | Mikus et al. | |
| 6,146,380 A | 11/2000 | Racz et al. | |
| 6,158,250 A | 12/2000 | Tibbals, Jr. et al. | |
| 6,171,249 B1 | 1/2001 | Chin et al. | |
| 6,190,383 B1 | 2/2001 | Schmaltz et al. | |
| 6,193,714 B1 | 2/2001 | McGaffigan et al. | |
| 6,211,153 B1 | 4/2001 | Garnick et al. | |
| 6,238,336 B1 | 5/2001 | Ouchi | |
| 6,254,601 B1 | 7/2001 | Burbank et al. | |
| 6,280,441 B1 | 8/2001 | Ryan | |
| 6,296,639 B1 | 10/2001 | Truckai et al. | |
| 6,306,129 B1 | 10/2001 | Little et al. | |
| 6,315,741 B1 | 11/2001 | Martin et al. | |
| 6,379,348 B1 | 4/2002 | Onik | |
| 6,405,732 B1 | 6/2002 | Edwards et al. | |
| 6,419,648 B1 | 7/2002 | Vitek et al. | |
| 6,419,653 B2 | 7/2002 | Edwards et al. | |
| 6,419,673 B1 | 7/2002 | Edwards et al. | |
| 6,425,867 B1 | 7/2002 | Vaezy et al. | |
| 6,432,067 B1 | 8/2002 | Martin et al. | |
| 6,447,477 B2 | 9/2002 | Burney et al. | |
| 6,463,331 B1 | 10/2002 | Edwards | |
| 6,482,203 B2 | 11/2002 | Paddock et al. | |
| 6,485,413 B1 | 11/2002 | Boppart et al. | |
| 6,506,154 B1 | 1/2003 | Ezion et al. | |
| 6,506,156 B1 | 1/2003 | Jones et al. | |
| 6,506,171 B1 | 1/2003 | Vitek et al. | |
| 6,507,747 B1 | 1/2003 | Gowda et al. | |
| 6,508,815 B1 | 1/2003 | Strul et al. | |
| 6,522,142 B1 | 2/2003 | Freundlich | |
| 6,540,677 B1 | 4/2003 | Angelsen et al. | |
| 6,543,272 B1 | 4/2003 | Vitek | |
| 6,550,482 B1 | 4/2003 | Burbank et al. | |
| 6,554,780 B1 | 4/2003 | Sampson et al. | |
| 6,559,644 B2 | 5/2003 | Froundlich et al. | |
| 6,569,159 B1 | 5/2003 | Edwards et al. | |
| 6,572,613 B1 | 6/2003 | Ellman et al. | |
| 6,589,237 B2 | 7/2003 | Woloszko et al. | |
| 6,592,559 B1 | 7/2003 | Pakter et al. | |
| 6,602,251 B2 | 8/2003 | Burbank et al. | |
| 6,610,054 B1 | 8/2003 | Edwards et al. | |
| 6,612,988 B2 | 9/2003 | Maor et al. | |
| 6,613,004 B1 | 9/2003 | Vitek et al. | |
| 6,613,005 B1 | 9/2003 | Friedman et al. | |
| 6,623,481 B1 | 9/2003 | Garbagnati et al. | |
| 6,626,854 B2 | 9/2003 | Friedman et al. | |
| 6,626,855 B1 | 9/2003 | Weng et al. | |
| 6,632,193 B1 | 10/2003 | Davison et al. | |
| 6,635,055 B1 | 10/2003 | Cronin | |
| 6,635,065 B2 | 10/2003 | Burbank et al. | |
| 6,638,275 B1 | 10/2003 | McGaffigan | |
| 6,638,286 B1 | 10/2003 | Burbank et al. | |
| 6,645,162 B2 | 11/2003 | Friedman et al. | |
| 6,645,202 B1 | 11/2003 | Pless et al. | |
| 6,652,516 B1 | 11/2003 | Gough | |
| 6,660,002 B1 | 12/2003 | Edwards et al. | |
| 6,660,024 B1 | 12/2003 | Flaherty et al. | |
| 6,663,624 B2 | 12/2003 | Edwards et al. | |
| 6,663,626 B2 | 12/2003 | Truckai et al. | |
| 6,666,833 B1 | 12/2003 | Friedman et al. | |
| 6,679,855 B2 | 1/2004 | Horn et al. | |
| 6,685,639 B1 | 2/2004 | Wang et al. | |
| 6,689,128 B2 | 2/2004 | Sliwa, Jr. et al. | |
| 6,692,490 B1 | 2/2004 | Edwards | |
| 6,701,931 B2 | 3/2004 | Sliwa, Jr. et al. | |
| 6,705,994 B2 | 3/2004 | Vortman et al. | |
| 6,712,815 B2 | 3/2004 | Sampson et al. | |
| 6,716,184 B2 | 4/2004 | Vaezy et al. | |
| 6,719,755 B2 | 4/2004 | Sliwa, Jr. et al. | |
| 6,728,571 B1 | 4/2004 | Barbato | |
| 6,730,081 B1 | 5/2004 | Desai | |
| 6,735,461 B2 | 5/2004 | Vitek et al. | |
| 6,743,184 B2 | 6/2004 | Sampson et al. | |
| 6,746,447 B2 | 6/2004 | Davison et al. | |
| 6,764,488 B1 * | 7/2004 | Burbank et al. | 606/51 |
| 6,773,431 B2 | 8/2004 | Eggers et al. | |
| 6,790,180 B2 | 9/2004 | Vitek | |
| 6,805,128 B1 | 10/2004 | Pless et al. | |
| 6,805,129 B1 | 10/2004 | Pless et al. | |
| 6,813,520 B2 | 11/2004 | Truckai et al. | |
| 6,832,996 B2 | 12/2004 | Woloszko et al. | |
| 6,837,887 B2 | 1/2005 | Woloszko et al. | |
| 6,837,888 B2 | 1/2005 | Ciarrocca et al. | |
| 6,840,935 B2 * | 1/2005 | Lee | 606/34 |
| 6,936,048 B2 | 8/2005 | Hurst | |
| 6,994,706 B2 | 2/2006 | Chornenky et al. | |
| 7,517,346 B2 | 4/2009 | Sloan et al. | |
| 2001/0014805 A1 | 8/2001 | Burbank et al. | |
| 2001/0051802 A1 | 12/2001 | Woloszko et al. | |
| 2002/0002393 A1 | 1/2002 | Mitchell | |
| 2002/0022835 A1 | 2/2002 | Lee | |
| 2002/0052600 A1 | 5/2002 | Davison et al. | |
| 2002/0068871 A1 | 6/2002 | Mendlein et al. | |
| 2002/0077550 A1 | 6/2002 | Rabiner et al. | |
| 2002/0183735 A1 | 12/2002 | Edwards et al. | |
| 2003/0009164 A1 | 1/2003 | Woloszko et al. | |
| 2003/0014046 A1 | 1/2003 | Edwards | |
| 2003/0028111 A1 | 2/2003 | Vaezy et al. | |
| 2003/0130575 A1 | 7/2003 | Desai et al. | |
| 2003/0130655 A1 | 7/2003 | Woloszko et al. | |
| 2003/0195420 A1 | 10/2003 | Mendlein et al. | |
| 2003/0199472 A1 | 10/2003 | Al-Hendy et al. | |
| 2003/0216725 A1 | 11/2003 | Woloszko et al. | |
| 2003/0216759 A1 | 11/2003 | Burbank et al. | |
| 2004/0002699 A1 | 1/2004 | Ryan et al. | |
| 2004/0006336 A1 | 1/2004 | Swanson | |
| 2004/0030268 A1 | 2/2004 | Weng et al. | |
| 2004/0054366 A1 | 3/2004 | Davison et al. | |
| 2004/0120668 A1 | 6/2004 | Loeb | |
| 2004/0143252 A1 * | 7/2004 | Hurst | 606/41 |
| 2004/0153057 A1 | 8/2004 | Davison | |
| 2004/0175399 A1 | 9/2004 | Schiffman | |
| 2004/0176760 A1 | 9/2004 | Qiu | |
| 2004/0193028 A1 | 9/2004 | Jones et al. | |
| 2004/0215182 A1 | 10/2004 | Lee | |
| 2004/0230190 A1 | 11/2004 | Dahla et al. | |
| 2004/0254572 A1 | 12/2004 | McIntyre et al. | |
| 2005/0038340 A1 | 2/2005 | Vaezy et al. | |
| 2005/0085730 A1 * | 4/2005 | Flesch et al. | 600/459 |
| 2005/0107781 A1 | 5/2005 | Ostrovsky et al. | |
| 2005/0124882 A1 | 6/2005 | Ladabaum et al. | |
| 2005/0149013 A1 | 7/2005 | Lee | |
| 2005/0177209 A1 | 8/2005 | Leung et al. | |

| | | | |
|---|---|---|---|
| 2005/0197577 | A1 | 9/2005 | Makin et al. |
| 2005/0215990 | A1 | 9/2005 | Govari |
| 2005/0228288 | A1 | 10/2005 | Hurst |
| 2005/0255039 | A1 | 11/2005 | Desai |
| 2005/0256405 | A1 | 11/2005 | Makin et al. |
| 2006/0010207 | A1 | 1/2006 | Akerman et al. |
| 2006/0058680 | A1* | 3/2006 | Solomon .................... 600/466 |
| 2006/0178665 | A1 | 8/2006 | Sloan |
| 2006/0189972 | A1* | 8/2006 | Grossman .................... 606/32 |
| 2006/0241368 | A1* | 10/2006 | Fichtinger et al. ........... 600/407 |
| 2007/0006215 | A1 | 1/2007 | Epstein et al. |

FOREIGN PATENT DOCUMENTS

| | | |
|---|---|---|
| WO | WO 98/11834 | 3/1998 |
| WO | WO 98/14169 | 4/1998 |
| WO | WO 99/43366 | 9/1999 |
| WO | WO 00/00098 | 1/2000 |
| WO | WO 01/80723 A2 | 11/2001 |
| WO | WO 01/95819 A1 | 12/2001 |
| WO | WO 02/11639 A1 | 2/2002 |
| WO | WO 03/005882 A2 | 1/2003 |
| WO | WO 03/005882 A3 | 1/2003 |
| WO | WO 03/065908 A1 | 8/2003 |
| WO | WO 2004/002293 A2 | 1/2004 |
| WO | WO 2004/002550 A2 | 1/2004 |
| WO | WO 2004/020011 A1 | 3/2004 |
| WO | WO 2004/035110 A2 | 4/2004 |
| WO | WO 2004/058328 A2 | 7/2004 |
| WO | WO 2004/064658 | 8/2004 |

OTHER PUBLICATIONS

Bergamini et al., "Laparoscopic Radiofrequency Thermal Ablation: A New Approach to Symptomatic Uterine Myomas," *Am. J. Obstetrics and Gynecology* (2005) 192: 768-73.

CNN.com Health Women, "Experimental technique uses lasers to shrink uterine fibroids," Nov. 28, 2000.

Hindley et al.; "MRI guidance of focused ultrasound therapy of uterine fibroids: Early results," *American Journal of Roentgenology*, 2004, 183(6): 1173-1719.

Kanaoka et al., "Microwave endometrial ablation at a frequency of 2.45 Ghz. A pilot study," *J Reprod Med*. Jun. 2001; 46(60): 559-63.

Law et al., "Magnetic resonance-guided percutaneous laser ablation of uterine fibroids," *J Magn Reson Imaging*, Oct. 2000; 12(4):565-70.

Liu et al., "Catheter-Based Intraluminal Sonography," *J. Ultrasound Med.*, 2004, 23:145-160.

Mogami et al., "Usefulness of MR-guided percutaneous cryotheraphy," *Med. Imaging Technol*. 2004, 22(3): 131-6. (English abstract).

MSNBC OnLine Articles, About Us: Articles; "Intrauerine Fibroids Can Now Be Treated Nonsurgically".

Okamura et al., "Force Modeling for Needle Insertion into Soft Tissue," *IEEE Transactions on Biomedical Engineering*, Oct. 2001, 10 (51): 1707-1716.

RSNA 2000 Explore News Release; "Lasers Liquefy Uterine Fibroid Tumors," 11:30 a.m. CST, Monday, Nov. 27, 2000.

Senoh et al., "Saline Infusion Contrast Intrauterine Sonographic Assessment of the Endometrium with High-Frequency, Real-Time Miniature Transducer Normal Menstrual Cycle: a Preliminary Report," *Human Reproduction*, 14 (10): 2600-2603, 1999.

Vascular and Interventional Radiology, SRSC; *Nonsurgical Treatment of Uterine Fibroids*.

Websand, Inc., *New treatment options for fibroid tumors*, Copyright 2002 by WebSand, Inc.

* cited by examiner

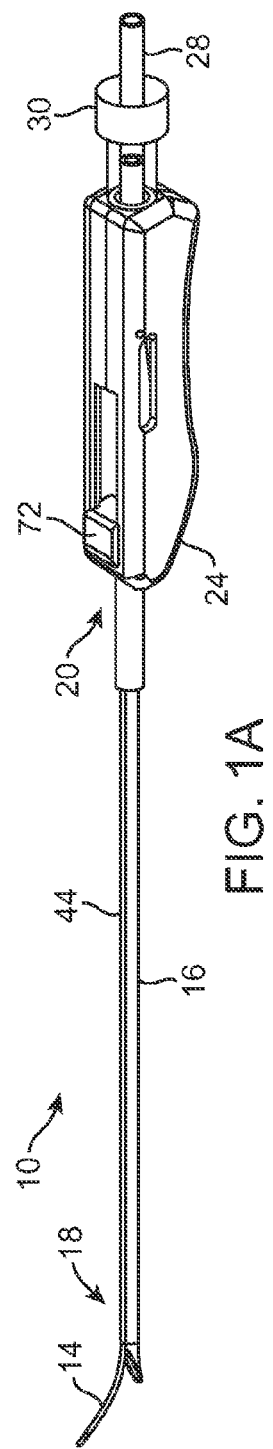
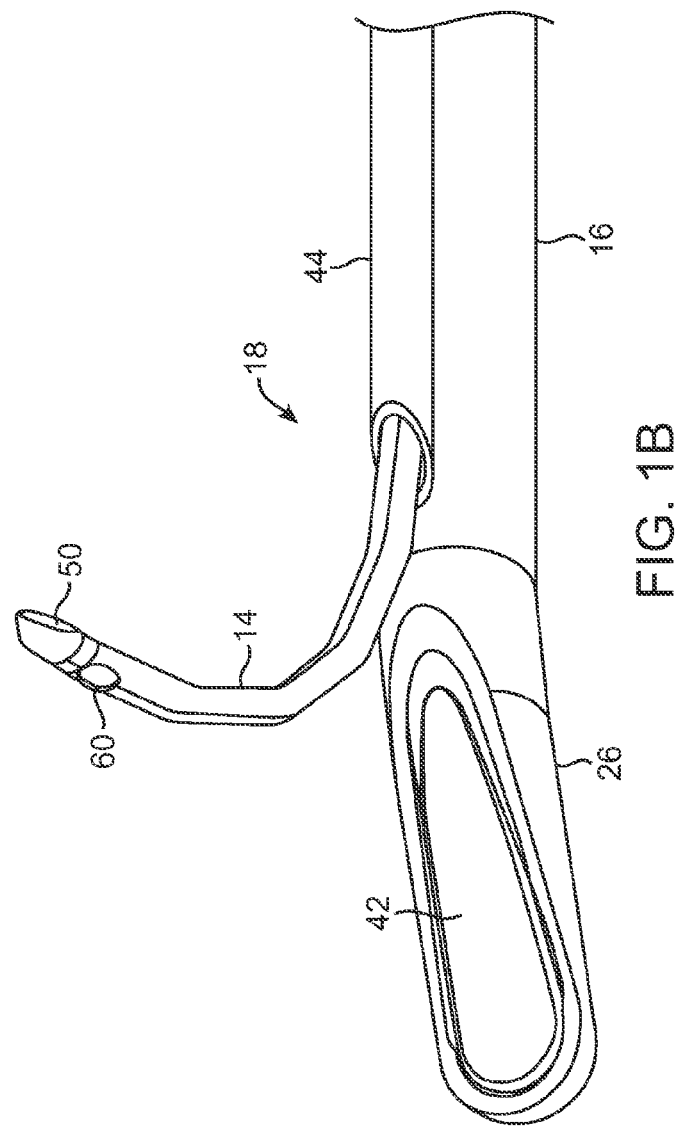
FIG. 1A
FIG. 1B

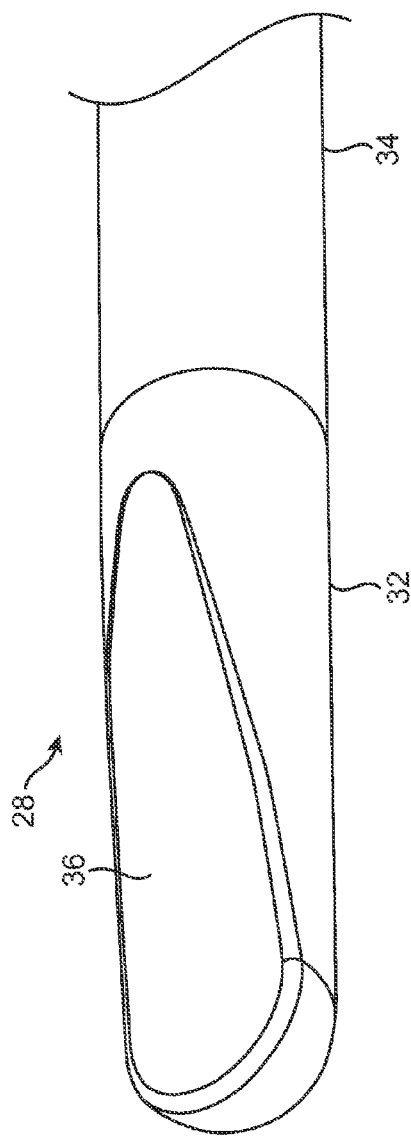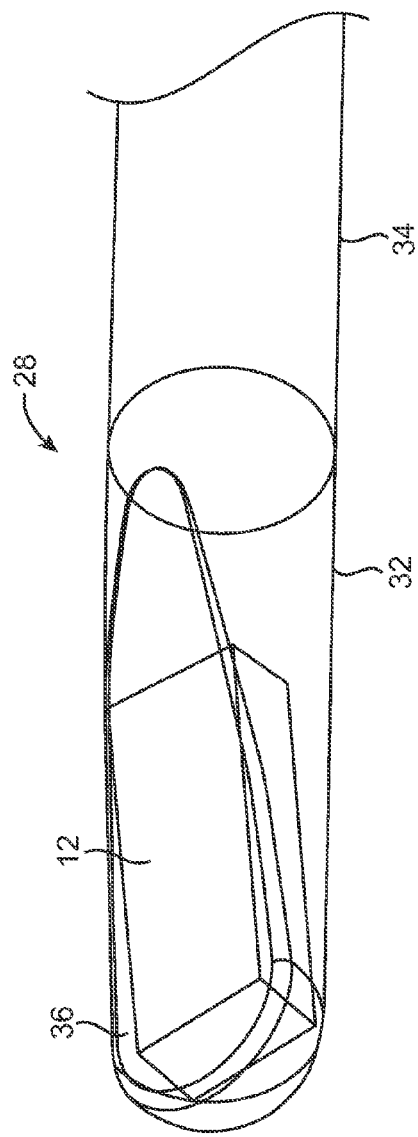
FIG. 2A
FIG. 2B

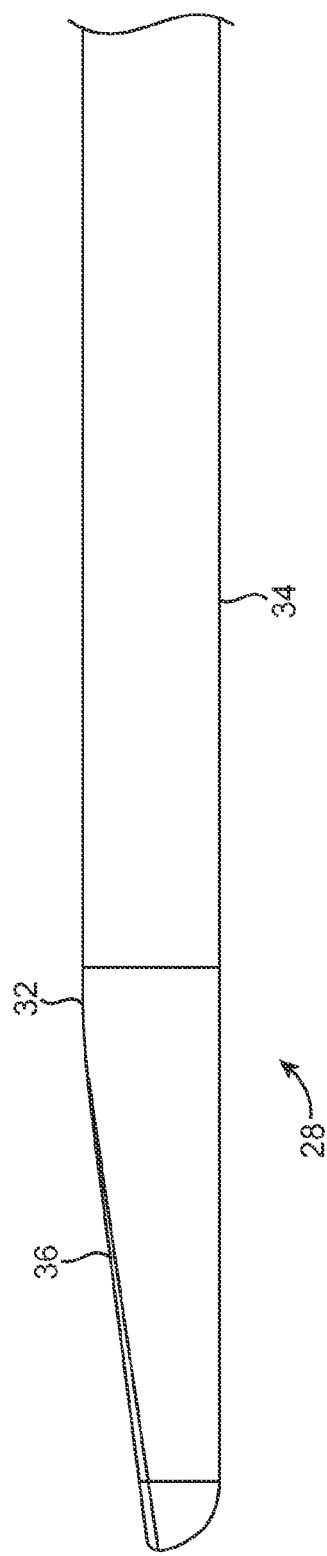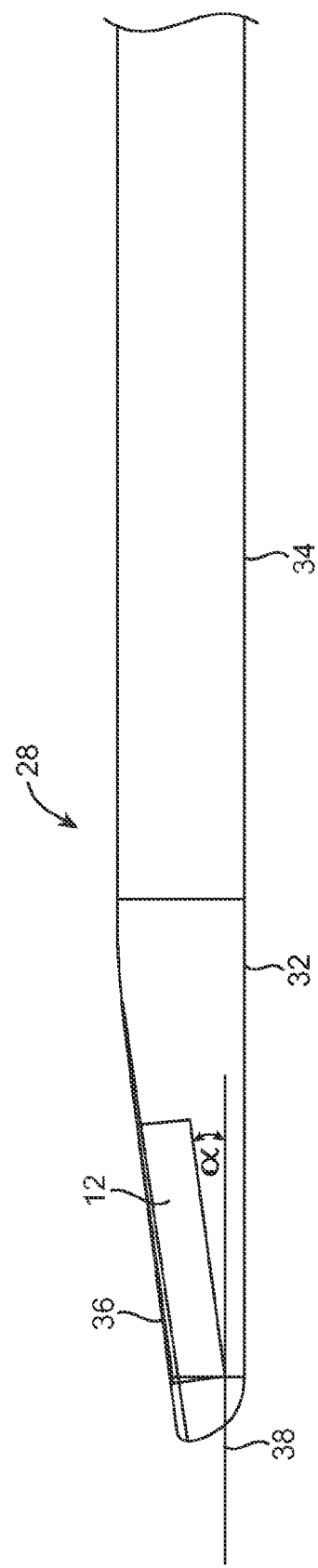

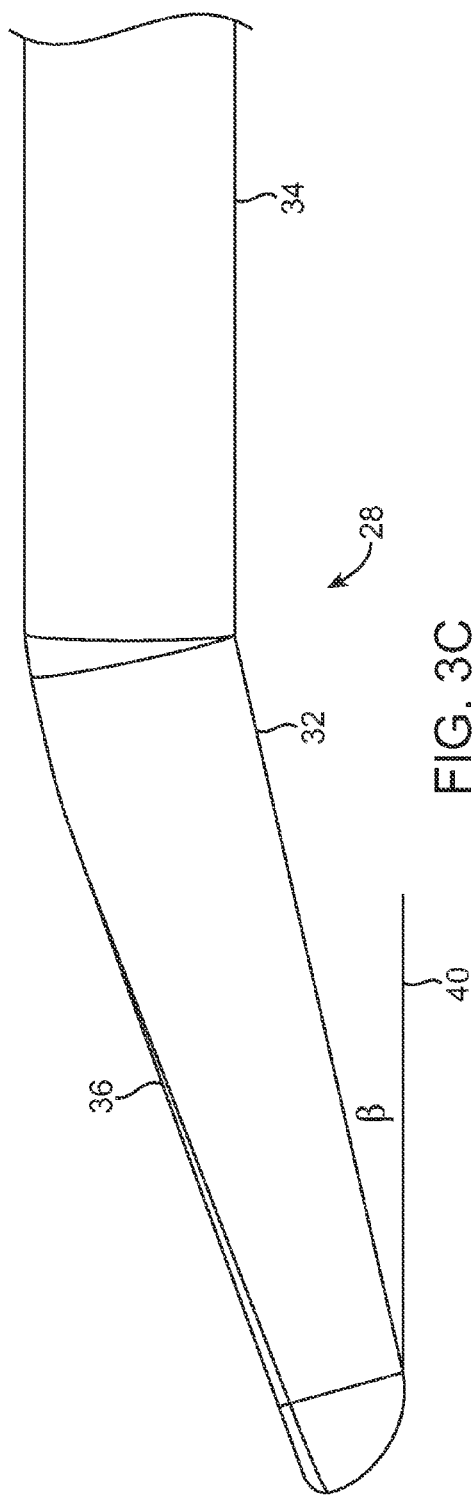
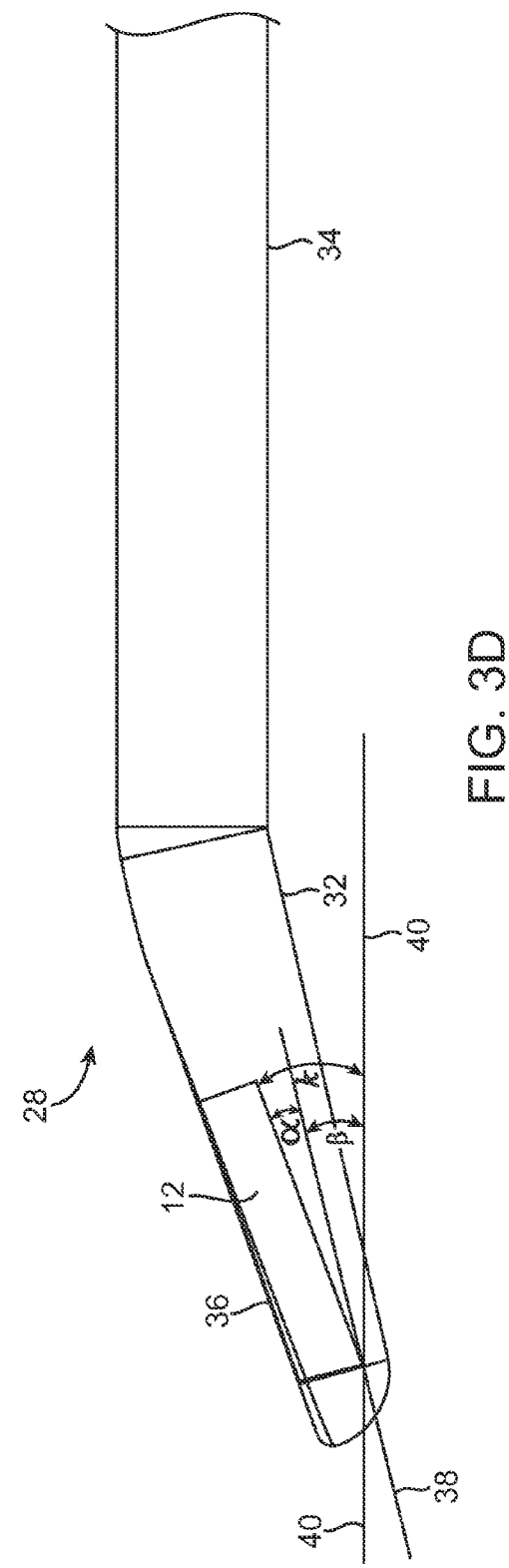

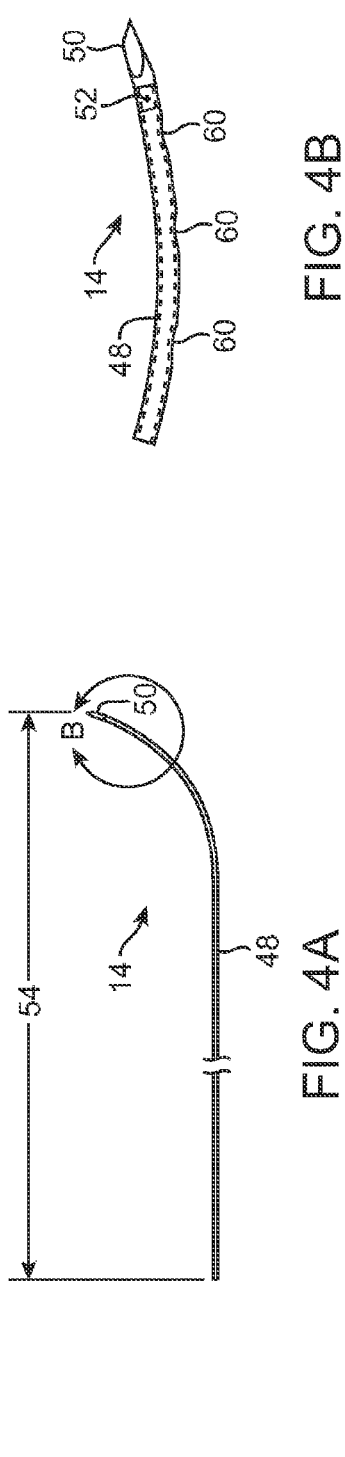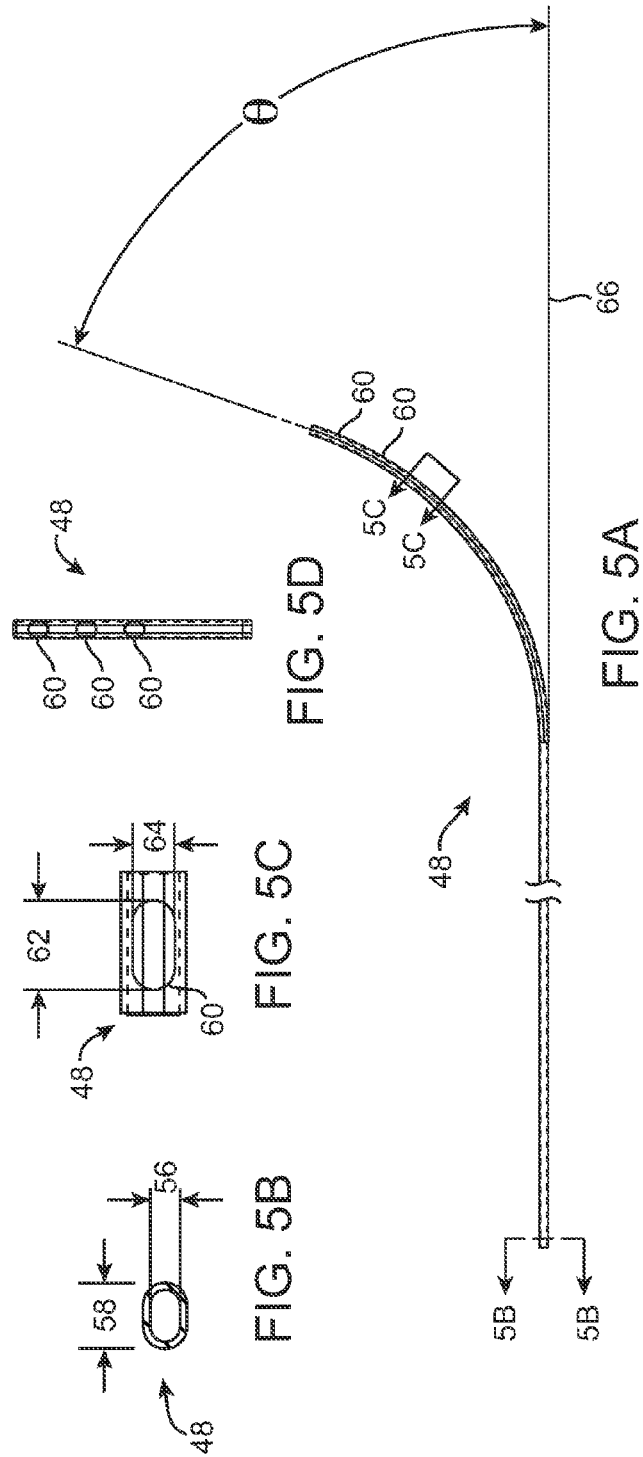

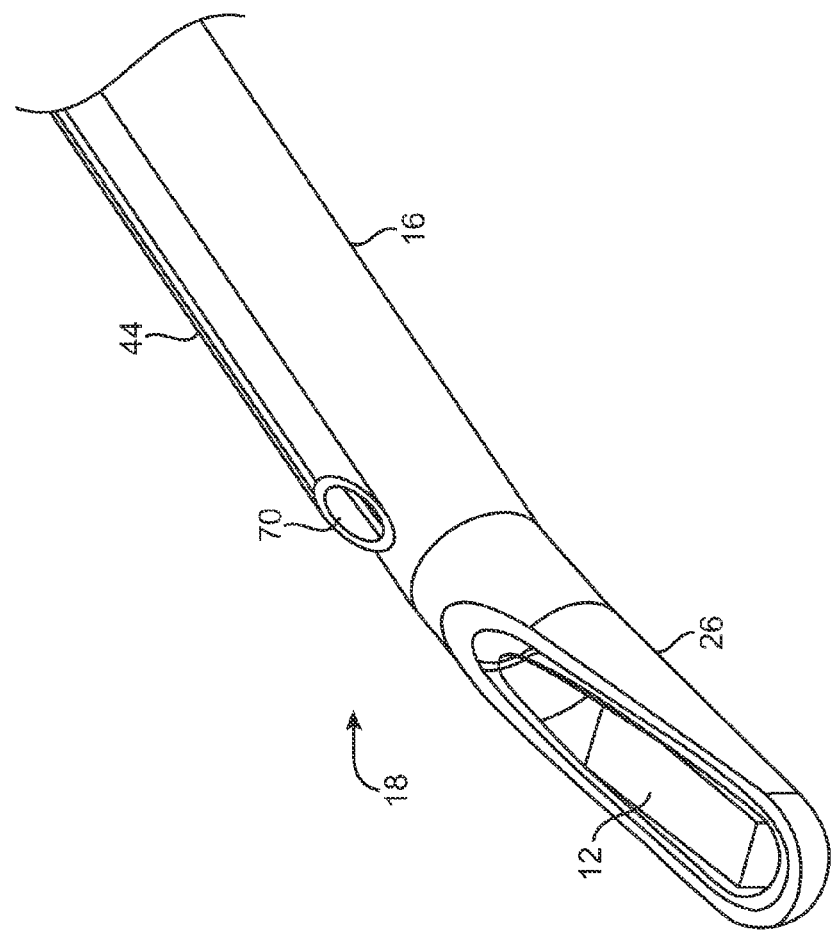
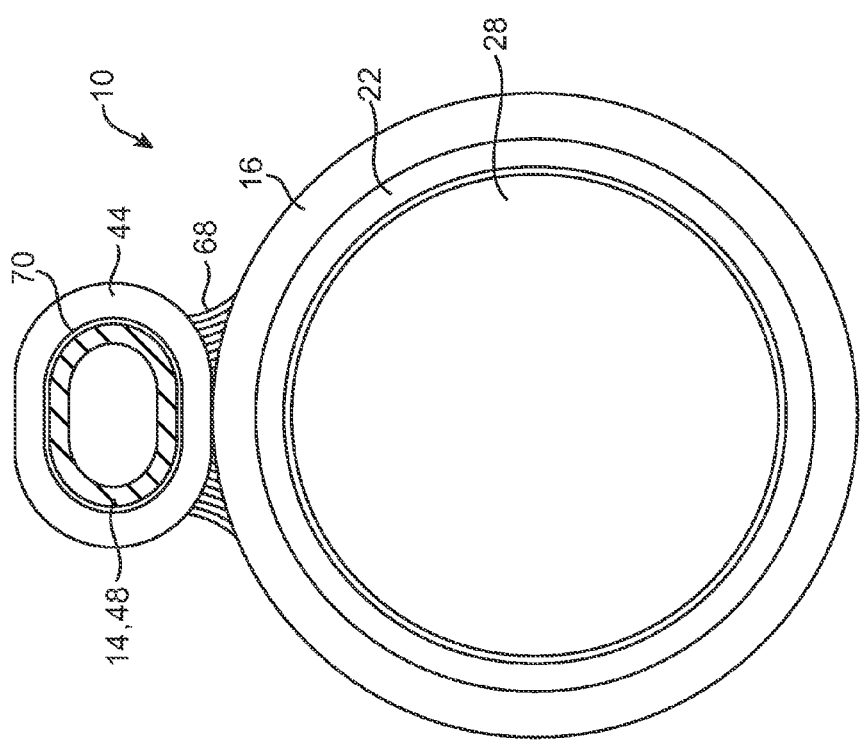
FIG. 8
FIG. 7

RIGID DELIVERY SYSTEMS HAVING INCLINED ULTRASOUND AND NEEDLE

BACKGROUND OF THE INVENTION

The present invention relates generally to medical systems and methods. More particularly, the invention relates to rigid delivery systems having an inclined ultrasound array for improved imaging and curved needle for ablation treatment and methods for using such systems.

Treatment of the female reproductive tract and other conditions of dysfunctional uterine bleeding and fibroids remain unmet clinical needs. Fibroids are benign tumors of the uterine myometrial (muscle) and are the most common tumor of the female pelvis. Fibroid tumors affect up to 30% of women of childbearing age and can cause significant symptoms such as discomfort, pelvic pain, mennorhagia, pressure, anemia, compression, infertility and miscarriage. Fibroids may be located in the myometrium (intramural), adjacent to the endometrium (submucosal) or in the outer layer of the uterus (subserosal). Most commonly fibroids are a smooth muscle overgrowth that arise intramurally and can grow to be several centimeters in diameter.

Current treatments for fibroids include both pharmacological therapies and surgical interventions. Pharmacological treatment includes the administration of medications such as NSAIDS, estrogen-progesterone combinations, and GnRH analogues. All medications are relatively ineffective and are palliative rather than curative. Hysterectomy (surgical removal of the uterus) is another common treatment for fibroids. While effective, hysterectomy has many undesirable side effects such as loss of fertility, open surgery, sexual dysfunction and long recovery time. There is also significant morbidity (sepsis, hemorrhage, peritonitis, bowel and bladder injury), mortality and cost associated with hysterectomy. Surgical myomectomy, in which fibroids are removed, is an open surgical procedure requiring laparotomy and general anesthesia. Often these procedures and long with significant blood loss and can only remove a portion of the culprit tissue.

To overcome at least some of the problems associated with open surgical procedures, laparoscopic myomectomy was pioneered in the early 1990's. However, laparoscopic myomectomy remains technically challenging, requiring laparoscopic suturing which limits its performance to only the most skilled of laparoscopic gynecologists. Other minimally invasive treatments for uterine fibroids include hysteroscopy, uterine artery ablation, endometrial ablation, and myolysis.

Hysteroscopy is the process by which a thin fiber optic camera is used to image inside the uterus and an attachment may be used to destroy tissue. Hysteroscopic resection is a surgical technique that uses a variety of devices (loops, roller balls, bipolar electrodes) to ablate or resect uterine tissue. The uterus needs to be filled with fluid for better viewing and thus has potential side effects of fluid overload. Hysteroscopic ablation is limited by its visualization technique and is thus only appropriate for those fibroids that are submucosal and/or protrude into the uterine cavity.

Uterine artery embolization was introduced in the early 1990's and is performed through a groin incision by injecting small particles into the uterine artery to selectively block the blood supply to fibroids. Complications include pelvic infection, premature menopause and severe pelvic pain. In addition, long term MRI data suggest that incomplete fibroid infarction may result in regrowth of infarcted fibroid tissue and symptomatic recurrence.

Endometrial ablation is primarily a procedure for dysfunctional (or abnormal) uterine bleeding and may be used at times for fibroids. Endometrial ablation relies on various energy sources such as cryo energy, microwave energy and radiofrequency energy. Endometrial ablation destroys the endometrial tissue lining the uterus but does not specifically treat fibroids. This technique is also not for women who desire future childbearing. Endometrial ablation remains an excellent therapy for dysfunctional uterine bleeding but is limited in its ability to treat fibroids.

Myolysis was first performed in the 1980's using lasers or RF energy to coagulate tissue, denature proteins and necrose myometrium with laparoscopic visualization. Laparoscopic myolysis can be an alternative to myomectomy, as the fibroids are coagulated and then undergo coagulative necrosis resulting in a dramatic decrease in size. As with all laparoscopic techniques, myolysis treatment is limited by the fact that it can only allow for visualization of subserosal fibroids.

Needle myolysis uses a laparoscope or open technique to introduce one or more needles into a fibroid tumor under direct visual control. Bipolar or unipolar radio frequency ("RF") current, cryo energy, or microwave energy is then delivered between two adjacent needles, or unipolar current between a single needle and a distant dispersive electrode affixed to the thigh or back. The aim of needle myolysis is to coagulate a significant volume of the tumor and thereby cause it to shrink substantially. The traditional technique is to make multiple passes through different areas of the tumor using the coagulating needle to destroy many cylindrical cores of abnormal tissue. However, the desirability of multiple passes is mitigated by the risk of adhesion formation, which is thought to increase with increasing amounts of injured uterine serosa, and by the operative time and skill required. Myolysis can be an alternative to myomectomy, as the fibroids are coagulated and then undergo coagulative necrosis resulting in a dramatic decrease in size. Myolysis is generally limited by the fact that it is used with direct visualization and can therefore only see (and therefore treat) subserosal fibroids.

To overcome the limitations of current techniques, it would be desirable to provide a minimally invasive approach to selectively eradicate fibroid tumors within the uterus. A solution in the treatment of fibroid tumors that combines imaging and ablation in one simple hand held system is needed. It would be further desirable if the system and method could locate and treat all types of fibroids in the uterus in a safe and effective manner with minimum risk and discomfort for the patient. It would be still further desirable if the systems could employ multiple interchangeable components both to permit selective sterilization or re-use of the components and to permit the system to be configured individually for patients having different anatomies and needs. It would be still further desirable if such systems could provide for improved imaging (e.g., enhanced field of view) and variability in the curved needle for ablation treatment. At least some of the objections will be met by the inventions described below.

BRIEF SUMMARY OF THE INVENTION

The present invention provides a rigid delivery system having an inclined ultrasound array for improved imaging and curved needle for ablation treatment. The system allows for needle deployment into solid tissue under direct, usually real-time, visualization and/or ultrasound visualization. Typically, the needle will be deployed from within a natural or created body cavity or body lumen. Exemplary body cavities include the uterus, the esophagus, the stomach, the bladder, the colon, and the like. Exemplary body lumens include the ureter, the urethra, fallopian tubes, and the like. Created body cavities include insufflated regions in the abdomen, the thoracic cavity, regions around joints (for arthroscopic procedures), and the like. The present invention will generally not find use with procedures in blood vessels or other regions of the vasculature. Thus, while the following description will be directed particularly at procedures within the uterus for detecting and treating uterine fibroids, the scope of the present invention is not intended to be so limited.

In a first aspect of the present invention, a rigid delivery system comprises a rigid delivery shaft, an imaging core, and an interventional core. The rigid delivery shaft will have a proximal end, a distal end, and an axial passage. The axial passage will typically extend the entire length of the shaft from the proximal to distal end and be open at least at the proximal end. The shaft will usually be rigid along all or a portion of its length, but in other instances may be flexible, deflectable, or steerable. The imaging core preferably comprises an ultrasound imaging insert or probe disposed within the axial passage, usually being removably disposed so that it may be removed and replaced to permit sterilization and re-use. The imaging insert will have an ultrasound array within a distal portion thereof, wherein the ultrasound array is tilted relative to a shaft axis so as to provide an enhanced field of view, as discussed in more detail below. The ultrasound array may be tilted at an angle in a range from about 7 degrees to about 15 degrees, preferably in a range from about 7 degrees to about 10 degrees. It will be appreciated that the interventional core may be adapted for any conventional form of medical imaging, such as optical coherence tomographic imaging, direct optic visualization, and as such is not limited by ultrasonic imaging.

The ultrasound imaging insert further comprises a flat viewing window disposed over the ultrasound array at the distal portion. The distal end of the rigid shaft further comprises a mechanical alignment feature, as for example a flat viewing surface, for axial or rotational orientation of the ultrasound imaging insert within the shaft. The flat viewing surface will be visually transparent to permit imaging from within the axial passage by the imaging insert. It will be appreciated however that the transparent visualization window which aids in physical alignment does not have to be visually transparent for ultrasound. For example, at least a portion of the flat viewing surface may be composed of an ultrasonically translucent material to permit ultrasonic imaging though the surface of the shaft. Further, the re-usable ultrasound imaging insert may be acoustically coupled to the outer delivery shaft to ensure that the ultrasound energy effectively passes from one component to the other. Ultrasonic acoustic coupling may be accomplished in several ways by one or a combination of means, including a compliant material (e.g., pad, sheet, etc.), fluid (e.g., water, oil, etc.), gel, or close mechanical contact between the rigid shaft and ultrasound imaging insert.

The rigid delivery shaft preferably has a deflectable or fixed pre-shaped or pre-angled distal end. The delivery shaft distal end may be deflected or bent at an angle in a range from about 0 degrees to about 80 degrees relative to the shaft axis, preferably in a range from about 10 degrees to about 25 degrees. The ultrasound imaging insert will usually be flexible (and in some instances deflectable or steerable) so that the distal portion of the ultrasound imaging insert is conformable or bendable to the same angle as the shaft deflectable distal end. The cumulative effect of array tilting and shaft bending advantageously provide an enhanced viewing angle of the ultrasound imaging insert, which is in a range from about 7 degrees (i.e., angle due to tilted ultrasound array) to about 90 degrees relative to the shaft axis. In a preferred embodiment, the viewing angle is about 20 degrees, wherein the array tilting and shaft bending are at about 10 degrees respectively. It will be appreciated that several geometries of array tilting and shaft bending may be configured so as to provide the desired viewing angle (e.g., distally forward direction, side-viewing or lateral direction), as for example viewing of end on views within the uterus (e.g., cornua and fundus).

The interventional core preferably comprises a curved needle coupled to the rigid shaft via a needle guide. Significantly, an angle of needle curvature is dependent upon (e.g., inversely proportional to) the ultrasound array tilt and the shaft bend. For example, an increase in an angle of array tilting or shaft bending decreases an angle of needle curvature. This in turn provides several significant advantages such as allowing a treating physician or medical facility to selectively choose an appropriate needle curvature based upon such indications (e.g., variability in needle curvature). Further, a decrease in the angle of needle curvature provides for enhanced pushability, deployability, and/or penetrability characteristics as well as simplified manufacturing processes. The angle of needle curvature may be in a range from about 0 degrees to about 80 degrees relative to an axis, preferably the angle is about 70 degrees when the viewing angle is about 20 degrees. The curved needle generally comprises a two-piece construction comprising an elongate hollow body and a solid distal tip. The solid tip may comprise an asymmetric or offset trocar tip. For example, the tip may comprise a plurality of beveled edges offset at a variety of angles. It will be appreciated that the needle may take on a variety of geometries in accordance with the intended use including those described in co-pending U.S. patent application Ser. No. 11/347,018, filed Feb. 2, 2006, which is assigned to the assignee of the present application and incorporated herein by reference.

The needle guide will be attachable to an outer surface of the shaft and have a guide passage isolated from the axial passage so as to prevent any interference between the imaging insert and ablating needle. The curved needle may be removably and replaceably disposed within the guide passage. The guide passage will typically extend approximately the entire length of the shaft and be open at least at the distal end so as to allow the needle to be reciprocatably deployed and penetrated into adjacent solid tissue. Preferably, the curved needle and needle guide have a flattened oval shape that has a wideness that is greater than a thickness. This oval cross sectional shape is intended to inhibit lateral deflection during deployment or penetration of the needle.

In another aspect of the present invention, a delivery system includes a shaft, an imaging core, and an interventional core. The delivery shaft has a proximal end, an angled distal tip, and an axial passage therethrough. The imaging core comprises an ultrasound imaging insert disposed within the axial passage. The imaging insert has an ultrasound array within a distal portion thereof, wherein the ultrasound array is tilted relative to a shaft axis. The interventional core comprises a curved ablation needle coupled to the shaft. An angle of needle curvature may be inversely proportional to the ultrasound array tilt and tip angle.

As discussed above, the geometries of the shaft, imaging insert, treatment needle, and needle guide may be varied in accordance with the intended use. The delivery shaft, ultrasound imaging insert, treatment needle, and/or needle guide may be integrally formed or fixed with respect to one another or preferably comprise separate, interchangeable modular components that are coupleable to one another to permit selective sterilization or re-use and to permit the system to be configured individually for patients having different anatomies and needs. For example, a sterilizable and re-usable ultrasound insert may be removably positioned within a disposable shaft. An exemplary interventional deployment and imaging system is described in more detail in co-pending U.S. Provisional Patent Application Ser. No. 60/758,881, filed Jan. 12, 2006, which is assigned to the assignee of the present application and incorporated herein by reference.

In yet another aspect of the present invention, a method for using an imaging and needle deployment system as described herein is provided. The method comprises inserting a rigid shaft having a proximal end, a distal end, and an axial passage therethrough within a uterus. The distal end of the rigid shaft may then be selectively deflected. An ultrasound imaging insert may then be loaded within the axial passage prior to, concurrent with, or subsequent to shaft insertion, wherein a distal portion of the insert conforms to the deflected shaft distal end. Loading may further involve axially or rotationally aligning the ultrasound imaging insert within the rigid shaft. A needle curvature is then selected by the physician or medical facility from a plurality of needles (i.e., at least two or more) having different curvatures based on at least an angle of the deflected shaft distal end. The selected curved needle is then loaded along the rigid shaft.

The ultrasound array may be tilted or inclined within the distal portion of the insert, wherein selecting the needle curvature further comprises accounting for the ultrasound array tilt. As described above, the ultrasound array is preferably tilted at an angle in a range from about 7 degrees to about 10 degrees relative to a shaft axis. Deflecting will typically comprise pulling a pull or tensioning wire coupled to the shaft distal end in a proximal direction. Deflection occurs at an angle in a range from about 0 degrees to about 80 degrees relative to the shaft axis, wherein the needle curvature is in a range from about 0 degrees to about 90 degrees (i.e., in the case of a non-tilted ultrasound array) relative to an axis. The method further comprises imaging the uterus with a viewing angle of the ultrasound array in a range from about 0 degrees to about 90 degrees (i.e., in the case of a straight needle) relative to the shaft axis, wherein the viewing angle is based upon the deflected shaft distal end and the tilted ultrasound array. It will be appreciated that torquing and/or rotating the rigid device in addition to tip deflection and ultrasound tilt will allow a physician to obtain the desired viewing plane.

Methods further include ablating a uterine fibroid within the uterus with the selected curved needle. In those cases, the needle may be a radiofrequency (RF) electrode, a microwave antenna, a cryogenic probe, or other energy delivery or mediating element intended for ablating or otherwise treating tissue. The distal tip of the needle will usually be adapted so that it will self-penetrate into the tissue as it is advanced from the needle guide. The direction of advancement will be coordinated with the imaging field of the ultrasound insert so that the penetration of the curved needle can be viewed by the physician, usually in real time. Further, an electrolyte (e.g., saline) or other agent may be infused within the uterus prior to or concurrently with fibroid ablation so as to enhance the therapeutic effect provided by the treatment needle. This is preferably accomplished by providing at least one or more (e.g., two, three, four, five, etc.) infusion holes or apertures on the needle body. In still other cases, the needle could be a hollow core needle intended for sampling, biopsy, otherwise performing a diagnostic procedure.

A further understanding of the nature and advantages of the present invention will become apparent by reference to the remaining portions of the specification and drawings.

BRIEF DESCRIPTION OF THE DRAWINGS

The following drawings should be read with reference to the detailed description. Like numbers in different drawings refer to like elements. The drawings, which are not necessarily to scale, illustratively depict embodiments of the present invention and are not intended to limit the scope of the invention.

FIGS. 2A through 2D illustrate exploded views of the distal portion of the ultrasound imaging insert of FIG. 1A in a straight configuration.

FIGS. 3A through 3D illustrate exploded views of the distal portion of the ultrasound imaging insert of FIG. 1A in a bent configuration.

FIGS. 4A and 4B illustrate the curved ablation needle of FIG. 1A comprising a hollow tube body and an asymmetric solid distal tip.

FIGS. 5A through 5D further illustrate the curved hollow tube body of FIG. 4A.

FIG. 7 illustrates a cross sectional view of the system of FIG. 1A.

FIG. 8 illustrates the system of FIG. 1A without the curved ablation needle.

DETAILED DESCRIPTION OF THE INVENTION

Figure 1C:
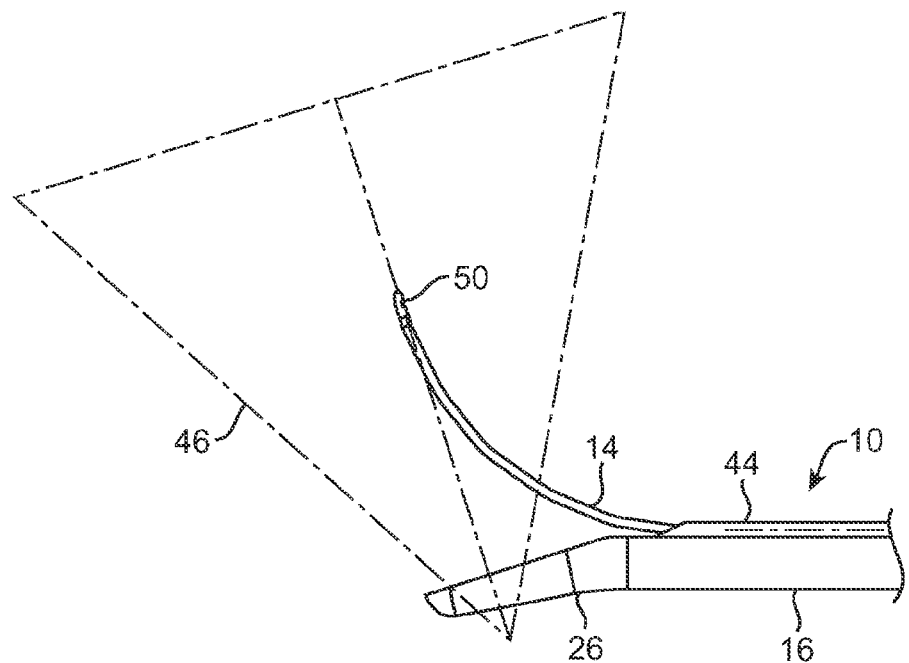
FIGS. 1A trhough 1D illustrate an exemplary rigid delivery system having an inclined ultrasound array for improved imaging and curved needle for ablation treatment constructed in accordance with the principles of the present invention.

Referring now to FIGS. 1A through 1D, an exemplary deflectable tip delivery system 10 having an inclined ultrasound array 12 for improved imaging and curved needle 14 for ablation treatment is illustrated. The system 10 generally includes a rigid delivery shaft 16, an ultrasound imaging insert 28, and a curved needle 14. The delivery shaft 16 comprises a distal end 18, a proximal end 20, and an axial passage 22. A handle 24 may be attachable to the proximal end 20 of the shaft 16. The distal end 18 of the shaft 16 may have a bent or deflectable distal tip 26, as best seen in FIGS. 1B and 1C. The ultrasound imaging insert 28 may be removably and replaceably disposed within the axial passage 22 of the shaft 16, as best seen in FIG. 7. A sealing element 30 may be provided between the ultrasound imaging insert 28 and the shaft handle 24 to ensure sufficient sealing around the insert 28 at a proximal end. It will be appreciated that the above depictions are for illustrative purposes only and do not necessarily reflect the actual shape, size, or dimensions of the system 10. This applies to all depictions hereinafter.

Referring now to FIGS. 2A through 2D, exploded views of a distal portion 32 of the ultrasound imaging insert 28 are illustrated. FIGS. 2A and 2C show isometric and side views respectively of the ultrasound imaging insert 28 in a straight position prior to insertion into the axial passage 22 of the delivery shaft 16, as will be described in more detail below. The ultrasound imaging insert 28 comprises a flexible shaft 34 and includes an ultrasound array 12 and a flat viewing window 36 within the distal portion 32. FIGS. 2B and 2D illustrate transparent isometric and side views respectively of the ultrasound imaging insert 28, wherein the ultrasound array 12 is shown tilted relative to the shaft axis 38. Preferably, the ultrasound array 12 is tilted or inclined at an angle α in a range from about 7 degrees to about 15 degrees. It will be appreciated that the angle α of inclination of the ultrasound array 12 may comprise a variety of angles (e.g., 0 degrees to about 45 degrees) as permitted by an outer diameter of the flexible shaft 34. The ultrasonic transducers 12 may be arranged in a phased array, for example either a linear phased array or a circumferential phased array. Alternatively, the ultrasonic imaging element 12 may comprise one or more independent elements, such as parabolic or other shaped imaging elements. In still further embodiments, the ultrasonic imaging transducers 12 may be arranged in a rotating mechanism to permit rotational scanning.

Figure 3A:
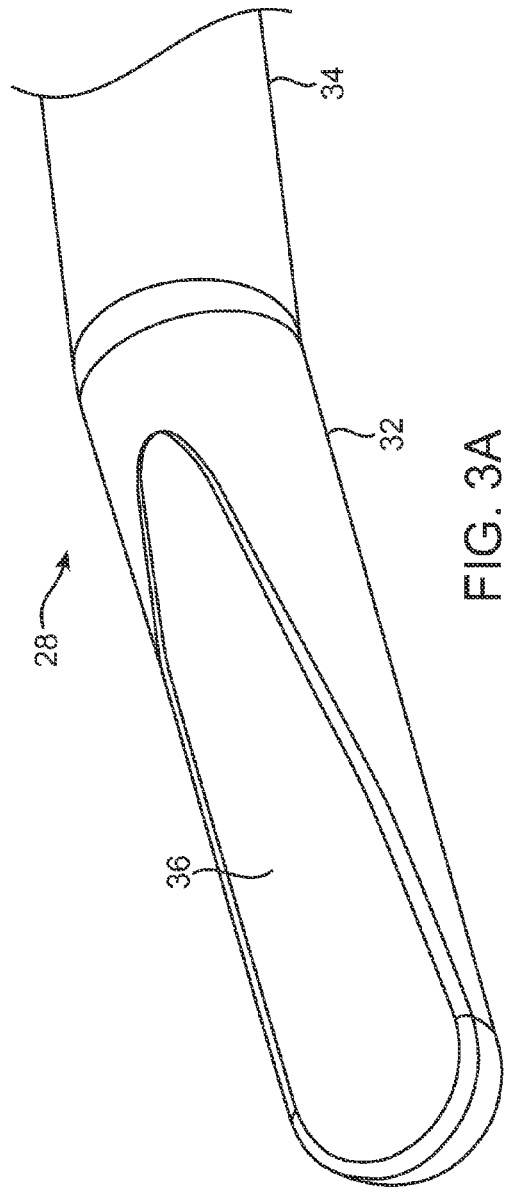
Figure 3B:
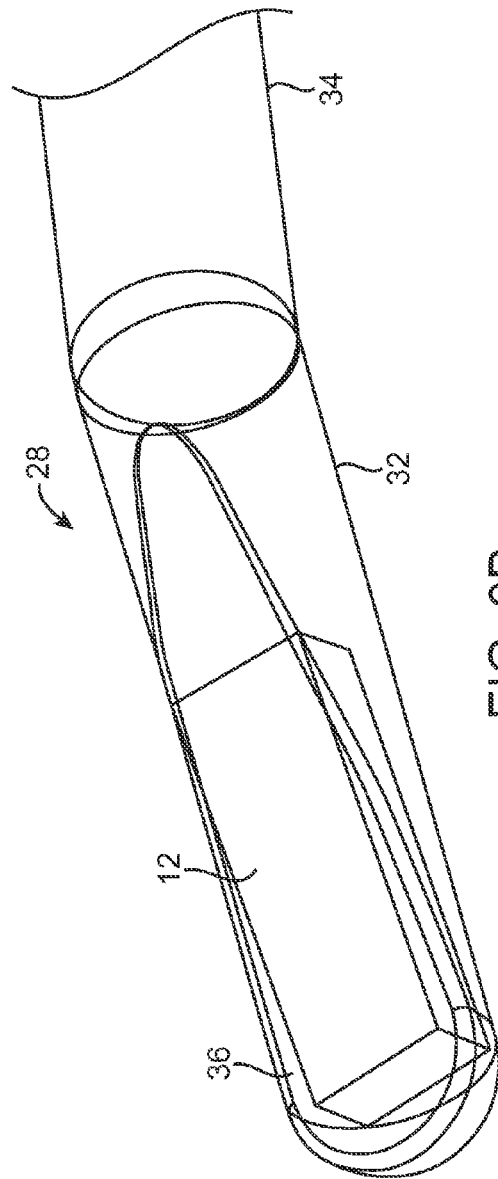

Referring now to FIGS. 3A through 3D, exploded views of a distal portion 32 of the ultrasound imaging insert 28 are further illustrated. FIGS. 3A and 3C show isometric and side views respectively of the ultrasound imaging insert 28 in a bent position subsequent to insertion into the axial passage 22 of the delivery shaft 16. In particular, the transparent isometric and side views of FIGS. 3B and 3D illustrate the cumulative effect of tilting the ultrasound array 12 relative to the shaft axis 38 at the angle α and bending the distal portion 32 of the ultrasound imaging insert 28. The bend angle β may be in a range from about 0 degrees to about 80 degrees relative to the shaft axis 40, preferably in a range from about 10 degrees to about 13 degrees. The bend angle β will be determined by the deflectable distal tip 26 of the delivery shaft 16 as the flexible insert 28 conforms to the deflectable distal tip 26 upon insertion within the shaft 16. The viewing angle κ of the ultrasound imaging insert 28 achieved by this cumulative effect may be in a range from about 7 degrees (i.e., angle due solely to tilted ultrasound array 12) to about 90 degrees relative to the shaft axis 40. In the illustrated embodiment, the viewing angle is about 20 degrees, wherein the array tilting is approximately 7 degrees and shaft bending is about 13 degrees.

Referring back to FIGS. 1B through 1D, the distal end 18 of the rigid shaft 16 may further comprise a viewing surface 42 having a flat inner surface for axial and/or rotational orientation of the ultrasound imaging insert 28 within the shaft 16. In particular, a treating physician may locate the flat viewing window 36 on the insert 28 with the flat transparent viewing surface 42 so that the insert comes into rotational orientation with said viewing surface. Further, the shaft 16 and the ultrasound imaging insert 28 may be acoustically coupled in several ways to ensure that the ultrasound energy effectively passes from one component to the other. For example, the ultrasound insert 28 may be placed in close mechanical contact with the shaft 16 so as to provide a dry coupling. In addition or alternatively, a thin compliant layer (e.g., pad or sheet) may be disposed between the viewing windows 36, 42 of the ultrasound insert 28 and the shaft 16 so as to provide further interference between such components. It will be appreciated that a thinner layer may be preferred due to considerations of unwanted acoustic losses, index of refraction, impedance and/or other material property effects. Still in addition to or alternatively, an inner cavity 22 between the shaft 16 and ultrasound imaging insert 28 may be filled with a fluid (e.g., water or oil) or gel to further provide a wet coupling which may compensate for any mechanical tolerances.

Figure 1D:
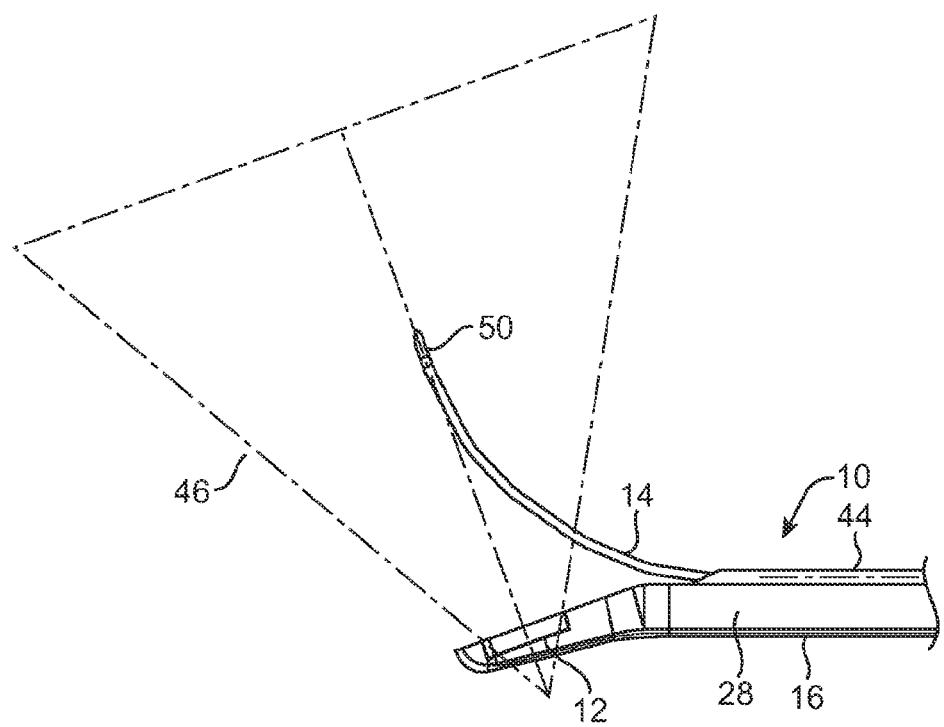

The shaft 16 of the present invention as described herein may serve several functions including delivering ultrasound, diagnostic, and/or interventional treatments, bending of the ultrasound insert via the deflectable distal tip, and/or providing a sterile barrier between the ultrasound and/or interventional components. As shown in FIG. 1D, the delivery shaft 16 carries the ultrasound imaging insert 28 within its axial passage 22. The viewing plane 46 provided by the tilted and bent ultrasound array 12 is further illustrated. Generally, the shaft 16 will have a length in a range from about 20 cm to about 40 cm and an outer diameter in a range from about 3 mm to about 10 mm, while the ultrasound imaging insert 28 will have a length in a range from about 50 cm to about 90 cm and an outer diameter in a range from about 2 mm to about 4 mm. Further, a needle guide 44 may be attachable to an outer surface of the shaft 16 for reciprocatably receiving the ablation/infusion needle 14, which is shown in an extended configuration and described in more detail below.

Referring now to FIGS. 4A and 4B, the curved needle 14 generally comprises a two-piece construction comprising an elongate hollow body 48 and a solid distal tip 50. The distal tip 50 may be laser welded 52 to the hollow tubular body 48 as shown in FIG. 4B. The tip 50 may also be attached via alternative means, for example adhesives or mechanical features or fits. The tubular body 48 is further illustrated in FIGS. 5A through 5D. The hollow tube 48 will have a length 54 in a range from about 20 cm to about 45 cm and an oval cross section having a thickness 56 in a range from about 0.5 mm to about 2 mm and a wideness 58 in a range from about 1 mm to about 3 mm. This flattened oval cross sectional shape as shown in FIG. 5B is intended to inhibit lateral deflection during deployment or penetration of the needle 14. FIGS. 5C and 5D illustrate three laser cut holes 60 within the tubular body 48 for the infusion of agents (e.g., electrolytes, drugs, etc.) so as to enhance the therapeutic effect of the needle 14 prior to or during ablation treatment. The infusion holes 60 may be aligned on one side of the tubular body 48 and have a length 62 in a range from about 0.5 mm to about 2 mm and a width 64 in a range from about 0.5 mm to about 2 mm.

As best seen in FIG. 5A, the hollow tubular body 48 may be curved at an angle θ in a range from about 0 degrees to about 80 degrees relative to an axis 66 so as to access side/lateral fibroids. In this depiction, the angle θ is about 70 degrees. Significantly, the angle of needle curvature 8 is dependent upon the ultrasound array tilt angle οα and the shaft bend angle β. For example, an increase in the tilt angle α or bend angle f decreases the angle of needle curvature 8. This in turn advantageously allows a treating physician to selectively choose an appropriate needle curvature from a plurality of needles 14 (i.e., at least two or more) having different curvature angles θ.

Figure 6A:
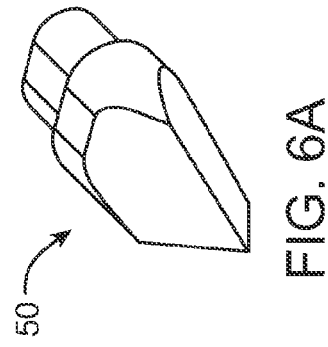
FIGS. 6A through 6E further illustrate the asymmetric solid distal tip of FIG. 4A.
Figure 6B:
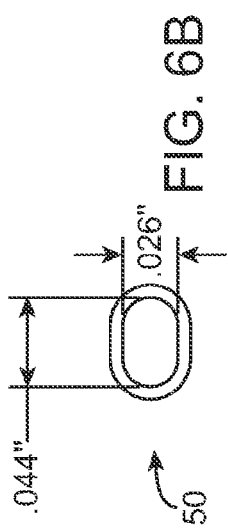
Figure 6C:
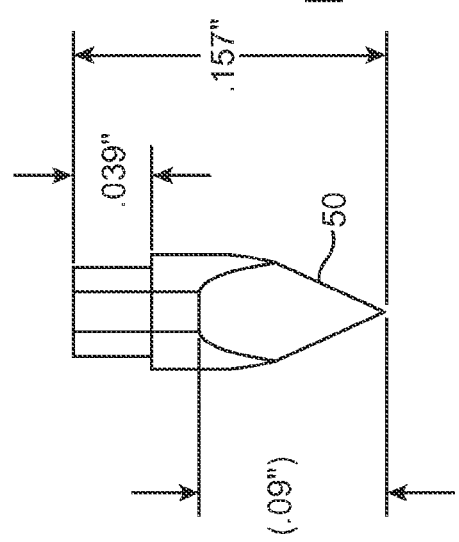
Figure 6D:
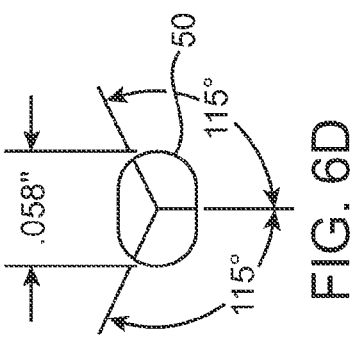
Figure 6E:
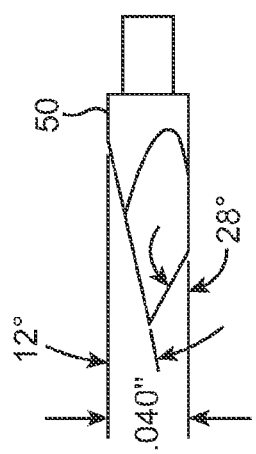

Referring now to FIGS. 6A through 6E, the solid tip 50 may comprise an asymmetric or offset trocar tip. The center point of the tip 50 may be offset from a centerline of the needle to help compensate for any needle deflections due to tenacious tissue, in effect steering the needle towards the intended target even with the deflection. For example, the tip 50 may comprise a plurality of beveled edges offset at a variety of angles as illustrated in FIGS. 6D and 6E. It will be appreciated that the solid tip 50 may comprise a variety of dimensions and shapes and is not limited to FIGS. 6A, 6B, 6C, 6D, and 6E. It will be further appreciated that the tip 50 need not be a separate component but may alternatively be integrally formed with the needle body 48. The needle 14, including the tip 50 and tubular body 48 may be formed from a variety of materials including stainless steel, nitinol, and like materials for transmitting ablation energy.

Referring now to FIG. 7, a cross sectional view of the system 10 is illustrated. As described above, the ultrasound imaging insert 28 is disposed within the axial passage 22 of the shaft 16. The needle guide 44 will be attachable to an outer surface of the shaft 16, such as with an adhesive 68 or other means such as laser welding, shrink tubing, and the like. It may also be integrally formed to the tube such as with an extrusion. The needle guide 44 will have a guide passage 70 isolated from the axial passage 22 so as to prevent any interference between the imaging insert 28 and ablating needle 14. The hollow needle 14, 48 may be removably and replaceably disposed within the guide passage 70. The needle guide 44 will typically have a length in a range from about 20 cm to about 40 cm and be attachable to the shaft handle 24 at a proximal end, usually just shorter than the shaft of the device. As best seen in FIG. 1A, the handle 24 may have a needle advancement button 72 to reciprocatably advance or retract the needle 14 from within the passage 70. The button 72 in this depiction is in a fully advanced position for complete deployment of the needle 14. The needle guide 44 will further have an oval cross section similar to that of the needle 14, with a thickness in a range from about 0.5 mm to about 2 mm and a wideness in a range from about 1 mm to about 3 mm. The flattened guide 44 and flattened needle 14 as shown in FIG. 7 are intended to inhibit lateral deflection during deployment or penetration of the needle 14.

Referring now to FIG. 8, the delivery 10 system without the curved ablation needle 14 is illustrated. The deflectable distal tip 26 of the rigid shaft 16 may be deflected by the use of pull or tensioning wire(s) housed within the shaft 16. Deflection may occur at a true mechanical pivot or at a flexible zone at the shaft distal end 18. As discussed above, when the delivery shaft 16 is deflectable by a user, various needles 14 may be used to match the amount of deflection provided by the distal tip 26 as well as the amount of tilt provided by the ultrasound array 12. Hence, the needle guide 44 will typically be empty until the distal end 18 of the shaft 16 is deflected. For example, the shaft 16 may be inserted in a straight configuration as illustrated in FIGS. 2A through 2D. The distal tip 26 may then be deflected until a target anatomy is identified. A needle 14 is then back loaded within the guide passage 70 that corresponds to the amount of the deflection.

Table I below illustrates possible viewing angles κ that may be achieved by the cumulative effects of the shaft bending angle β (e.g., either through active deflection of the distal tip or a pre-shaped or pre-bent distal tip) and the ultrasound tilting angle α. The matching needle angles θ based on the possible viewing angles κ are further illustrated. In example 1, the shaft 16 is in a straight configuration so that the viewing angle κ is provided solely by the tilting angle α of the ultrasound array 12. In example 4, the needle 14 will have a straight configuration. In example 5, a non-tilted and non-bent ultrasound array 12 version is covered. It will be appreciated that the viewing angle κ will be more than the bend angle β of the shaft 16 due to the additive effect of the tilting angle α of the ultrasound array 12. This allows the bend on the distal tip 26 of the shaft 16 to be shallower without compromising the cumulative viewing angle κ, which is of particular benefit for patient insertion considerations. In the case of a deflectable distal tip 26 in which insertion may be implemented in a straight configuration, the tiled ultrasound angle α still aids in reducing the needle angle θ.

TABLE I

| Example | Viewing Angle (κ) | Tilt Angle (α) | Bend Angle (β) | Needle Angle (θ) |
| --- | --- | --- | --- | --- |
| 1 | 7°-10° | 7°-10° | 0° | 80° |
| 2 | 20° | 7°-10° | 10°-13° | 70° |
| 3 | 45° | 7°-10° | 35°-38° | 45° |
| 4 | 90° | 7°-10° | 80°-83° | 0° |
| 5 | 0° | 0° | 0° | 90° |

Figure 9A:
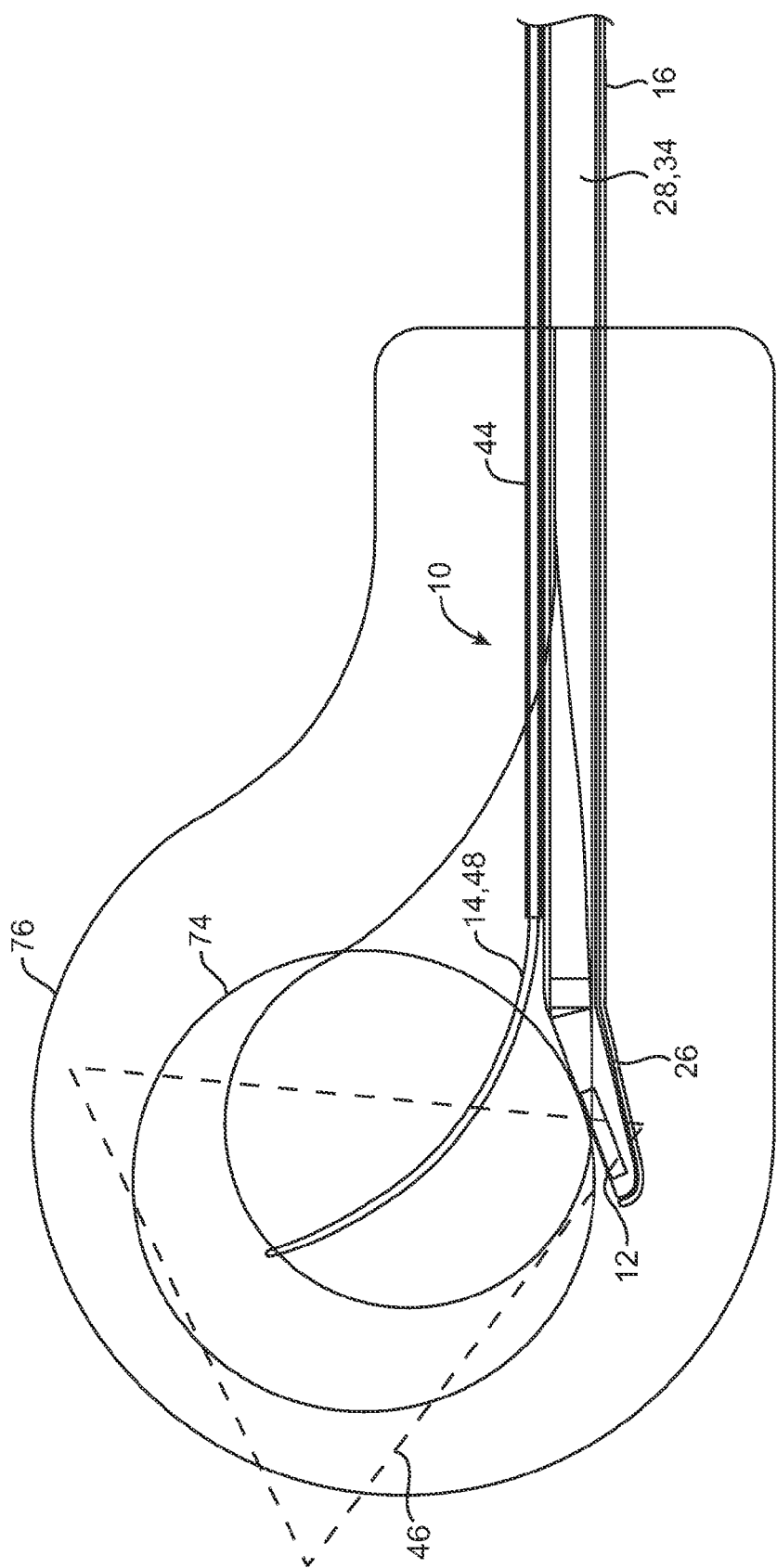
FIGS. 9A through 9C illustrate use of the system of FIG. 1A within a uterus for the treatment of fibroids in accordance with the principles of the present invention.
Figure 9B:
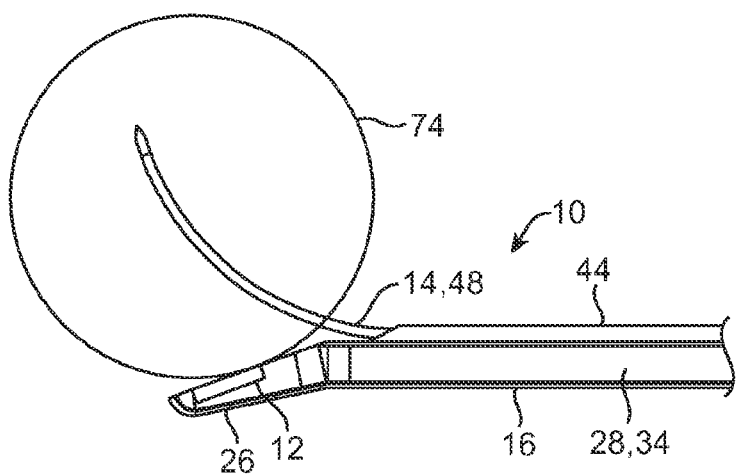
Figure 9C:
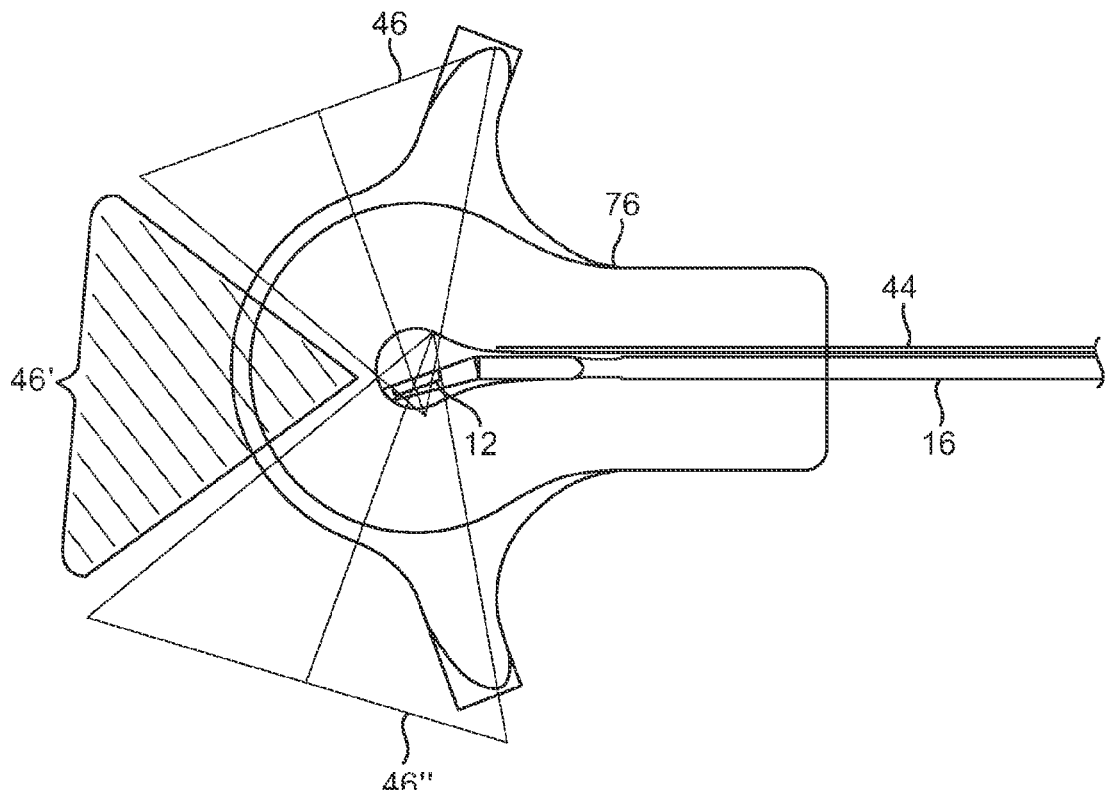

Referring now to FIGS. 9A and 9C, a method for using the system 10 of FIG. 1A to treat fibroids or tumors 74 within the uterus 76 is illustrated. Typically, the rigid shaft 16 is inserted in a straight configuration within the uterus 76. The distal tip 26 of the rigid shaft 16 may then be selectively deflected by a pull wire. The ultrasound imaging insert 28 may then be loaded within the axial passage 22 of the shaft 16 prior to, concurrent with, or subsequent to shaft 16 insertion, wherein a distal portion 32 of the insert 28 conforms to the deflected shaft distal end 26. Loading may further involve axially or rotationally aligning the ultrasound imaging insert 28 within the rigid shaft 16. A needle angle θ is then selected by the physician from a plurality of needles 14 having different curvatures based on the shaft bending angle β and the ultrasound tilting angle α. The selected curved needle 14 is then loaded within the passage 70 of the needle guide 44.

In exemplary embodiments, the therapeutic needle 14 advancement from the guide 44 via needle advancement button 72 on the shaft handle 24 can be viewed in real time as it is penetrated into the uterine fibroid 74 inside the uterus 76 as illustrated by the viewing plane 46 in FIGS. 9A and 9B. The therapeutic needle 14 may be penetrated in several configurations (e.g., lateral, side, axially extending) depending on the ultrasound viewing angle κ. Advantageously, tilting of the ultrasound array 12 and angling of the distal tip 26 allows a treating physician to image most or all of the cornua and fondus of the uterus 76 with a single device 10. As shown in FIG. 9C, the device 10 may be configured so as to provide the desired viewing angle κ (e.g., distally forward direction, side-viewing or lateral direction). It will further be appreciated that manipulation of the device 10, as for example, torquing and/or rotating the rigid device 16 in addition to tip deflection β and ultrasound tilt α will allow a physician to obtain the desired viewing planes 46, 46', 46". For example, viewing plane 46" may be achieved if the device 10 was rotated 180° about its axis. Further, viewing plane 46' may be achieved by torquing the device 10.

Although certain exemplary embodiments and methods have been described in some detail, for clarity of understanding and by way of example, it will be apparent from the foregoing disclosure to those skilled in the art that variations, modifications, changes, and adaptations of such embodiments and methods may be made without departing from the true spirit and scope of the invention. Therefore, the above description should not be taken as limiting the scope of the invention which is defined by the appended claims.

What is claimed is:

1. A rigid delivery system comprising:
   a rigid shaft having a proximal end, a distal end, a longitudinal axis, and a passage therethrough, wherein the passage has a closed distal end with ultrasonically transparent or translucent side viewing window having a flat inner surface being asymmetrically inclined relative to the longitudinal axis therein;
   an ultrasound imaging insert removably disposed within the passage and having an ultrasound array having a flat surface on a side thereof which flat surface aligns with the side viewing window when the insert is placed in the passage such that the flat surface of the ultrasound array contacts the flat inner surface of the shaft after the insert is fully received in the shaft, wherein the ultrasound array has a field of view with a center line which is tilted in a distally forward direction relative to the longitudinal axis and wherein the imaging insert may be removed and reused.

2. The system of claim 1, wherein the ultrasound array is tilted distally forwardly within the insert at an angle in a range from about 7 degrees to about 10 degrees relative to a longitudinal axis of the insert.

3. The system of claim 1, wherein the ultrasound imaging insert further comprises a flat viewing window disposed over the ultrasound array.

4. The system of claim 3, wherein the distal end of the rigid shaft further comprises a mechanical alignment feature for axial or rotational orientation of the ultrasound imaging insert with the closed-end passageway.

5. The system of claim 4, wherein the side viewing window of the rigid shaft comprises a flat viewing surface which aligns with the flat viewing window of the insert to align the insert when placed into the shaft.

6. The system of claim 1, wherein the rigid shaft has a deflectable or pre-shaped distal end.

7. The system of claim 6, wherein the shaft distal end is bent relative to the longitudinal axis of the shaft so that the center line is disposed at an angle in a range from about 10 degrees to about 25 degrees relative to the shaft axis.

8. The system of claim 7, wherein the angle is in a range from about 10 degrees to about 13 degrees.

9. The system of claim 7, wherein the ultrasound imaging insert is flexible.

10. The system of claim 9, wherein the distal portion of the ultrasound imaging insert is bent at the same angle as the shaft deflectable distal end.

11. The system of claim 6, further comprising a curved needle coupled to the rigid shaft.

12. The system of claim 11, wherein an angle of needle curvature is in a range from about 0 degrees to about 90 degrees relative to an axis.

13. The system of claim 12, wherein the angle is about 70 degrees.

14. The system of claim 11, wherein the curved needle comprises an elongate hollow body and a solid distal tip.

15. The system of claim 14, further comprising at least one infusion hole on the elongate hollow body.

16. The system of claim 14, wherein the solid distal tip comprises an asymmetric or offset trocar tip.

17. The system of claim 16, wherein the solid distal tip comprises a plurality of beveled edges offset at a variety of angles.

18. The system of claim 11, further comprising a needle guide attachable to an outer surface of the shaft and having a guide passage isolated from the axial passage, wherein the curved needle is disposed within the guide passage.

19. The system of claim 18, wherein the curved needle and needle guide have a flattened oval shape.

20. The system of claim 11, wherein the curved needle comprises a hollow core needle.

21. The system of claim 20, wherein the hollow core needle is adapted for performing biopsy.

22. The system of claim 20, wherein the hollow core needle is for performing a diagnostic procedure.

23. The system of claim 20, wherein the hollow core needle is adapted for performing sampling.

24. The system of claim 1, further comprising an acoustic coupling between the rigid shaft and ultrasound imaging insert.

25. The system of claim 24, wherein the acoustic coupling comprises a compliant material, fluid, gel, or close mechanical contact between the rigid shaft and ultrasound imaging insert.

26. A method for using an imaging and needle deployment system, said method comprising:
providing a rigid shaft having a proximal end, a distal end, a longitudinal axis, and an axial passage therethrough, wherein the passage has a closed distal end with an untrasonically transparent or translucent side window having a flat inner surface being asymmetrically inclined relative to the longitudinal axis therein, wherein the distal end of the rigid shaft is deflected relative to the longitudinal axis; and
loading an ultrasound imaging insert having an ultrasound array on a side thereof within the closed-end axial passage, wherein the ultrasound array has a flat viewing surface which aligns with the flat inner surface of the side viewing window on the rigid shaft such that the flat surface of the ultrasound array contacts the flat inner surface of the shaft after the insert is fully received in the shaft, and a distal portion of the insert conforms to the deflected shaft distal end so that a center line of a field of view of said ultrasound array is tilted in a distally forward direction relative to the longitudinal axis;
introducing the rigid shaft into a body cavity;
advancing a curved needle from the rigid shaft so that said needle passes across the tilted field of view and enters tissue while the needle is imaged with said imaging array;
removing the rigid shaft from the body lumen; and
removing the ultrasound imaging insert from the shaft to allow re-use of the insert.

27. The method of claim 26, wherein the ultrasound array is tilted distally forward relative to a longitudinal axis of the insert.

28. The method of claim 27, wherein the ultrasound array is tilted at an angle in a range from about 7 degrees to about 10 degrees relative to the longitudinal axis of the insert.

29. The method of claim 26, wherein the needle has a curvature selected so that said needle passes across the field of view.

30. The method of claim 26, wherein the shaft is deflected by pulling a pull wire coupled to the shaft distal end in a proximal direction.

31. The method of claim 26, wherein the distal end is deflected at an angle in a range from about 10 degrees to about 25 degrees relative to the longitudinal axis of the shaft.

* * * * *